United States Patent [19]

Beach

[11] 4,347,737
[45] Sep. 7, 1982

[54] HIGH TEMPERATURE OUTDOOR WEATHERING CHAMBER

[75] Inventor: Kenneth A. Beach, Canton, Mich.

[73] Assignee: Ford Motor Company, Dearborn, Mich.

[21] Appl. No.: 249,525

[22] Filed: Mar. 31, 1981

[51] Int. Cl.³ .......................................... G01N 25/00
[52] U.S. Cl. ..................................... 73/159; 374/57
[58] Field of Search .......... 73/150, 159, 15.4, 432 SD

[56] References Cited

U.S. PATENT DOCUMENTS

| | | | |
|---|---|---|---|
| 2,523,322 | 9/1950 | Ornstein et al. | 73/15.4 |
| 3,433,944 | 3/1969 | Truhan | 250/51 |
| 3,889,531 | 6/1975 | Suga | 73/150 R |

OTHER PUBLICATIONS

"Environmental Test Proposal" for Ford Motor Company by South Florida Test Service, 8 pages.

Primary Examiner—S. Clement Swisher
Attorney, Agent, or Firm—John J. Roethel; Clifford L. Sadler

[57] ABSTRACT

A high temperature outdoor weathering chamber approximating the passenger compartment of an automobile body for testing the effect of natural sunlight on material fibers and colors. The chamber comprises a box having insulated side and end walls and a hinged closure of standard automobile glass. The hinged glass closure provides access through the top of the box to a sample rack that is positioned below the glass closure to support samples for exposure to solar radiation.

An aluminum heat shield is positioned below the sample rack. The chamber is constructed and arranged so that air enters an air intake at the bottom of the box, flows through thermostatically controlled heater strips, then beneath the heat shield and out an exhaust outlet at the opposite end of the box above the level of the heat shield. Airflow is solely by convection.

5 Claims, 3 Drawing Figures

HIGH TEMPERATURE OUTDOOR WEATHERING CHAMBER

BACKGROUND OF THE INVENTION

The prior art is replete with apparatus for testing the effect of sunlight on textiles and other materials. By and large, most of the patentees utilize an artificial source of light to simulate sunlight. As disclosed in U.S. Pat. No. 3,433,944 issued Mar. 18, 1969, to Andrew Truhan for a "Radiant Energy Stability Test Chamber Having Air Circulating Means", the radiant energy producing means usually comprises, but is not limited to, fluorescent light, incandescent light, ultraviolet light, and combinations thereof.

It has been found, however, that it is not possible to accurately extrapole from the test results achieved under artificial light the degradation that will occur in textiles and other materials under actual conditions such as when the fabrics are used in the passenger compartment of an automobile body. It was apparent, however, there was a need for a controlled, high temperature test for vehicle body cloths and other materials for automotive interior applications. This test was not to be done with any laboratory apparatus equipped with an artificial light source. The materials had to be exposed to natural sunlight under glass in an enclosure approximating the passenger compartment of a standard size automobile.

After several years of discussion between representatives of the assignee of the present application and personnel of a firm having expertise in natural sunlight testing, certain criteria were established. The test chamber would have to be a black box having an insulated bottom, side and end walls and a closure for the top consisting of a hinged panel of standard automobile glass. A sample rack would have to be located beneath the glass and thermostatically controlled heater strips in the bottom of the box beneath the sample racks. Suspended between the heater strips and the sample rack would be a heat sink, preferably an aluminum sheet. Also, an air mixing system to level temperature distribution would be needed to some extent compensate for the wind chill factor and variations in cloud cover.

An object of this invention is to provide a test chamber that would meet the desired criteria and yet would have a simplified construction and arrangement that would provide the necessary conditions for the evaluation of the test samples.

SUMMARY OF THE INVENTION

The present invention relates to a high temperature outdoor weathering chamber approximating the passenger compartment of an automobile body. The chamber comprises a box that is open at the top and has insulated side and end walls. The top of the box has a hinged closure of standard automobile window glass. A sample rack is positioned within the box below the glass to support samples for exposure to natural sunlight. An aluminum heat shield is positioned below the sample rack to control the distribution of air through the box and to provide a heat sink. An air intake slot extends substantially across the width of the box at the base of one end wall. A strip heater means is mounted within the box contiguous to the one end wall between the air intake slot and the heat shield. A partition is provided for channeling airflow from the air intake slot through the strip heater means and then beneath the heat shield to an opening at one end of the latter in communication with an air exhaust outlet located in the opposite end wall of the box above the sample rack level. The airflow through the box is solely by convection. A thermocouple is mounted on the sample rack and a controller responsive to temperature changes in the box and sensed by the thermocouple controls the temperature input of the strip heater means to the chamber.

DESCRIPTION OF THE DRAWINGS

Other objects, advantages and features of the present invention will become more apparent as the description proceeds, reference being had to the accompanying drawings, wherein.

DETAILED DESCRIPTION OF THE INVENTION

Figure 1:
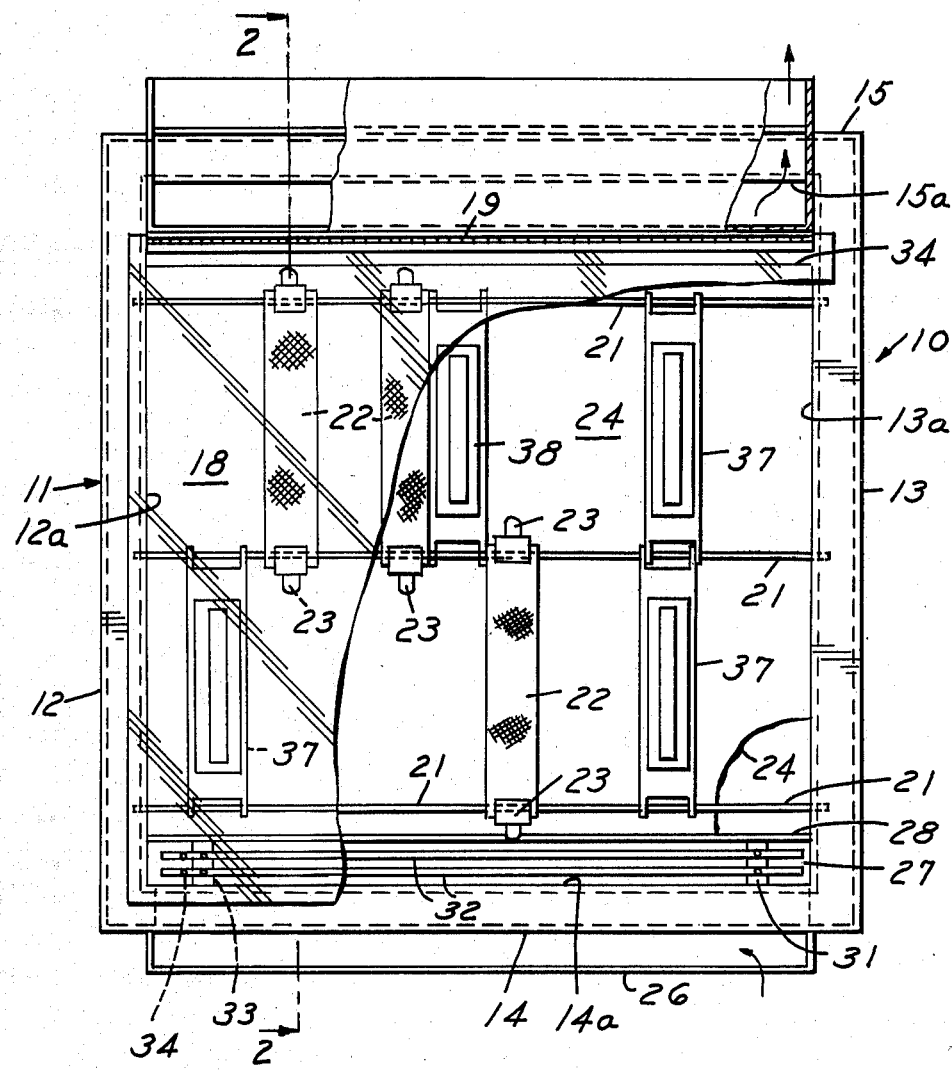
FIG. 1 is a plan view of the weathering chamber embodying the present invention.

Referring now to the drawings, the high temperature weathering chamber, generally designated 10, approximates a passenger compartment of a closed automobile body. It comprises a box 11 having a black interior. The hollow side walls 12 and 13, the end walls 14 and 15, and the bottom wall 16 are lined internally with insulating material 17 to minimize any heat loss through these walls. The open top of the box 11 is provided with a closure consisting of a sheet of standard automobile glass 18 hinged at one edge by conventional hinge devices 19 to the box. The opposite edge is provided with a lift handle 20.

A sample rack is positioned within the box 11 below the glass 18 to support samples for exposure to natural sunlight. Preferably, the sample rack comprises at least three parallel rods 21 extending laterally across the box 11 with the ends of the rods being anchored in the respective side walls 12 and 13. The plane of the sample rack 21 is located approximately three inches (76±7 mm) below the glass 18. If, for example, the material to be tested is a cloth, vinyl, or a cloth and vinyl combination, a suitable swatch or strip 22 is stretched between a pair of rods 21 and held thereon by suitable clips 23.

An aluminum sheet 24 is mounted within the box approximately half way between and in parallel spaced relationship to the sample rack rods 21 and the bottom wall 16 of the box. The aluminum sheet extends wall to wall between the side walls 12 and 13 of the box (see FIG. 3) and from the end wall 14 toward the end wall 15 but terminates short of the latter to provide an air gap therebetween (see FIG. 2). The sheet 24 has two functions, it controls the air flow through the box and also acts as a heat sink.

Figure 2:
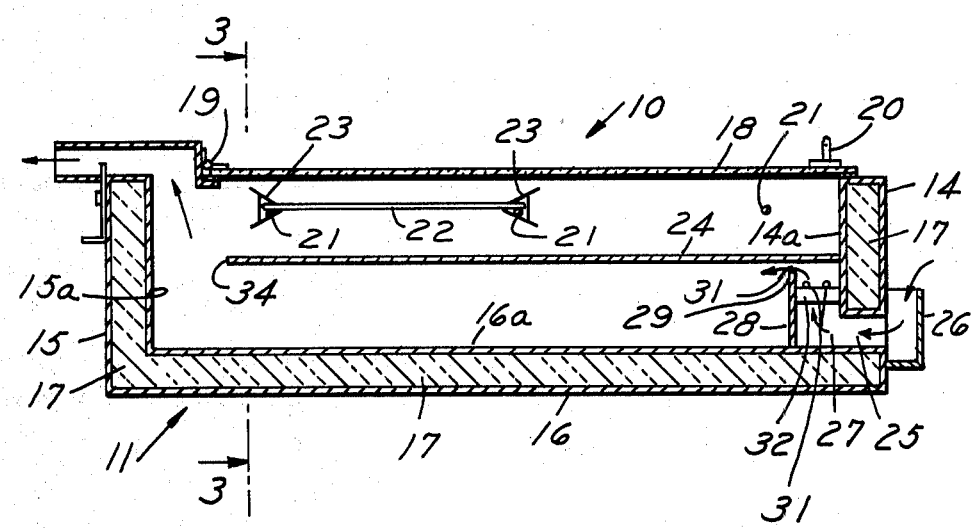
FIG. 2 is a section view on the line 2—2 of FIG. 1.
Figure 3:
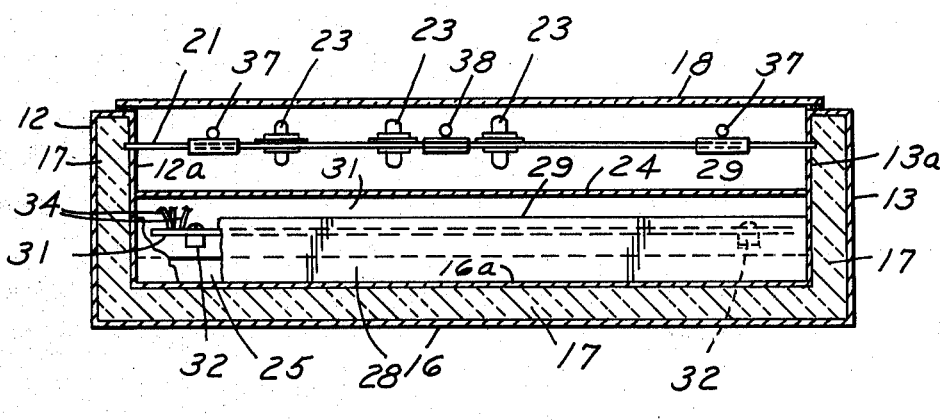
FIG. 3 is a section view of the line 3—3 of FIG. 2.

Air flow through the box is solely by convection. As best seen in FIG. 2, the box is provided with an air intake slot 25 at the base of the end wall 17. The slot 25 extends substantially across the width of the box. Preferably, an air deflector 26 is mounted on the external surface of the end wall 17 to prevent wind gusts from significantly varying the velocity of air being blown into the slot 25.

Air input into the box through the intake slot 25 enters a plenum chamber 27 formed by a partition or baffle 28 that extends across the width of the box. The upper edge 29 of the partition or baffle 28 is spaced from the underside of the heat shield 24 to provide an air gap 31 across the top of the partition. A plurality of heater strips 32, preferably two of them, are supported on bridge members 33 that extend between the end wall 14 of the box and the partition or baffle 28, the heater strips 32 extending the width of the box. The heater strips 32 vertically are located between the upper edge of the air intake slot 25 and the upper edge 29 of the partition 28.

The heater strips 32 are suitably bolted or clamped to the bridge members 33 and are provided with terminal clips 34 at one end for attachment to lead wires to a controller (not shown) for supplying electric current to the strips.

Air from the plenum chamber 27 through the gap 31 flows by convection on the underside of the heat shield 24 to the end 34 of the latter near the end wall 15 of the box and then ultimately finds its way out through an exhaust vent or slot 35 at the upper end of the end wall 15. An exhaust damper 36 may be manually set to control the size of the exhaust opening.

A plurality of thermocouples are positioned in various locations in the box. As best seen in FIG. 1, at least three thermocouples 37 preferably are supported on the sample rack rods 21 and are connected by suitable wires to conventional recording devices (not shown). Another thermocouple 38 also is positioned on the sample rack rods 21 and is located substantially in the center of one sample row. The thermocouple 38 is connected to the controller for turning on and off the electricity to the heater strips.

It will be understood that the temperature recording device and the controller may be located remotely from the location of the chamber 10. Following conventional practice, the test chamber preferably is mounted on a rack (not shown) that is adjustable to provide for seasonal exposure angle changes. That is, the test chamber is mounted so that the angle of exposure to the natural sunlight can be varied on a north/south axis to optimize solar irradiants.

In operation, it is preferable that the weathering chamber temperature be maintained at 88°±1° C. The test chamber is able to maintain this temperature because of the aluminum heat shield 24 that functions as a heat sink and because of the heater strips which are available to provide heat to compensate for the lack of solar irradiants caused by cloud cover over the test site or because of the lack of sunlight during the hours of darkness. Since airflow through the box is solely by convection, the cost of operation and maintenance of the box is minimal, as there are no fan motors or other moving parts subject to failure.

It is to be understood that this invention is not limited to the exact construction illustrated and described above, but that various changes and modifications may be made without departing from the spirit and scope of the invention as defined in the appended claims.

I claim:

1. A high temperature outdoor weathering chamber approximating the passenger compartment of an automobile body, comprising:
    a box open at the top and having insulated side and end walls;
    the top of the box having a hinged closure of standard automobile window glass;
    a sample rack positioned within the box below the glass to support samples for exposure to natural sunlight;
    an aluminum heat shield positioned below the sample rack to control the distribution of air through the box and to provide a heat sink;
    an air intake slot extending substantially across the width of the box at the base of one end wall;
    strip heater means mounted within the box contiguous to said one end wall and between the air intake slot and the heat shield;
    partition means for channeling airflow from the air intake slot through the strip heater means;
    the air then flowing beneath the heat shield to an opening at one end of the latter in communication with an exhaust air outlet located in the opposite end wall of the box above the sample rack level;
    the airflow through the box being solely by convection;
    a thermocouple mounted on the sample rack adapted to be coupled to a controller means to control the temperature input of the strip heater means.

2. A high temperature outdoor weathering chamber according to claim 1, in which:
    the partition means extends upwardly from the bottom of the box in substantially parallel relationship to said one end wall and terminates above the strip heater means in spaced relationship to the underside of the heat shield.

3. A high temperature outdoor weathering chamber according to claim 1 or 2, in which:
    the air exhaust slot parallels the upper edge of the box contiguous to the top of said opposite end wall.

4. A high temperature outdoor weathering chamber according to claim 3, in which:
    a damper means is provided at each end of the box to control airflow through the air intake slot and exhaust air outlet.

5. A high temperature outdoor weathering chamber according to claim 4, in which:
    a baffle extends across the outside of the box on the one end wall to moderate the flow of air into the box through the air intake slot.

* * * * *